United States Patent [19]

Hull et al.

[11] Patent Number: 4,463,433

[45] Date of Patent: Jul. 31, 1984

[54] PEDALLING EFFICIENCY INDICATOR

[75] Inventors: Maury L. Hull, Winter; Rory R. Davis, San Diego, both of Calif.

[73] Assignee: The Regents of the University of California, Berkeley, Calif.

[21] Appl. No.: 310,419

[22] Filed: Oct. 9, 1981

[51] Int. Cl.³ .................................................. G01L 5/02
[52] U.S. Cl. ..................................... 364/506; 73/379; 364/415
[58] Field of Search ....................... 364/413, 415, 506; 73/760, 788, 379; 128/630, 774, 25 B; 272/96, 73, DIG. 6

[56] References Cited

U.S. PATENT DOCUMENTS

| | | | |
|---|---|---|---|
| 3,845,663 | 11/1974 | Blomberg et al. | 73/379 |
| 3,967,503 | 7/1976 | Svensson | 73/379 |
| 4,141,248 | 2/1979 | Bargenda | 73/379 |
| 4,277,828 | 7/1981 | Tateishi | 364/415 |
| 4,375,674 | 3/1983 | Thornton | 364/413 |

Primary Examiner—Errol A. Krass
Attorney, Agent, or Firm—Fitch, Even, Tabin & Flannery

[57] ABSTRACT

A pedalling efficiency indicator measures the forces acting on the crank arm of a pedacycle to compute pedalling efficiency as a function of these forces. Generally, pedalling efficiency is computed as the ratio of the normal component of force acting on the crank arm to the resultant load of the crank arm. The computation of pedalling efficiency may then be visually indicated so that the pedacyclist may use a pedalling technique to maximize efficiency.

14 Claims, 11 Drawing Figures

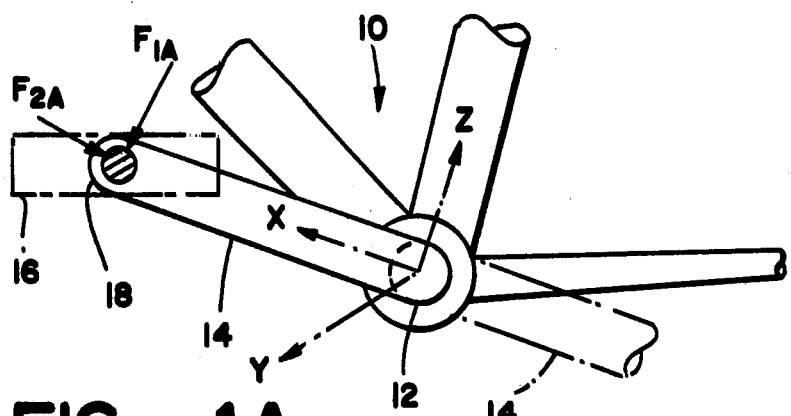
FIG_1A
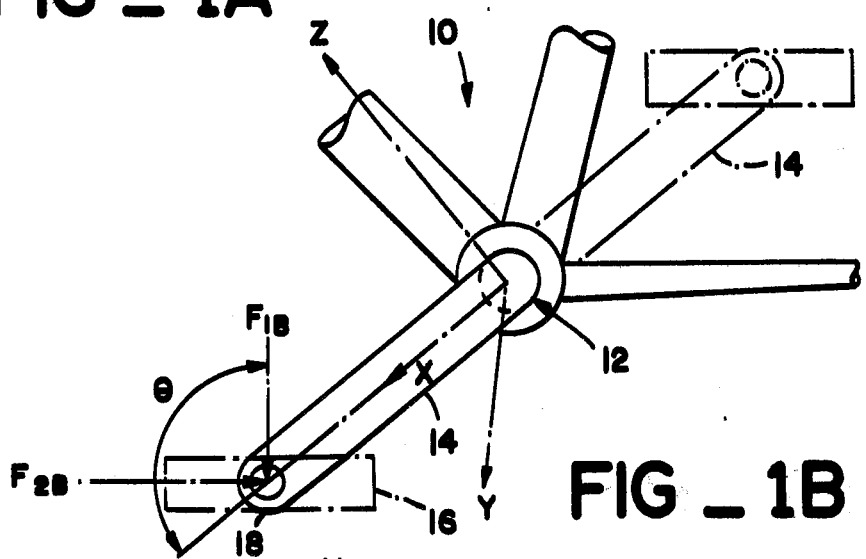
FIG_1B
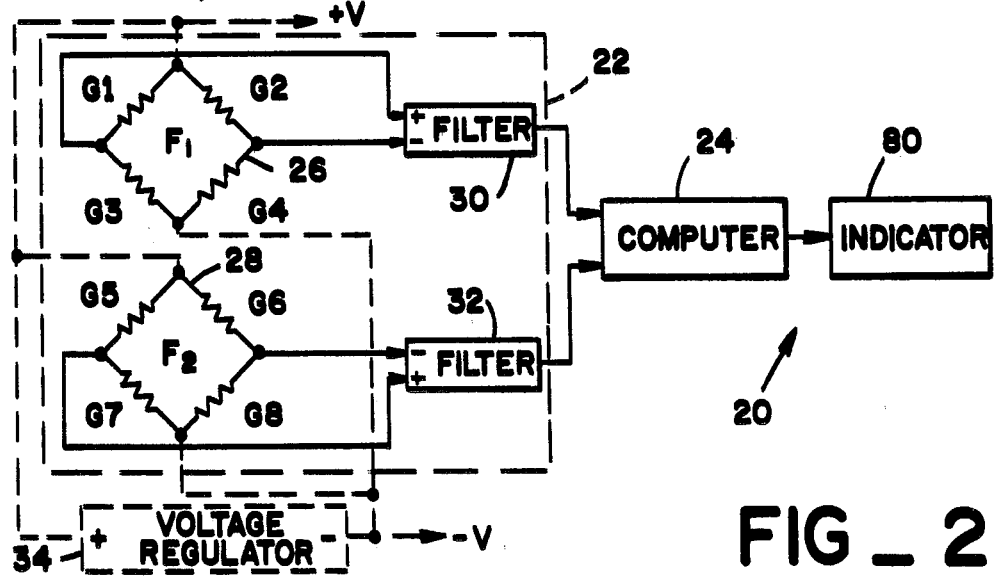
FIG_2

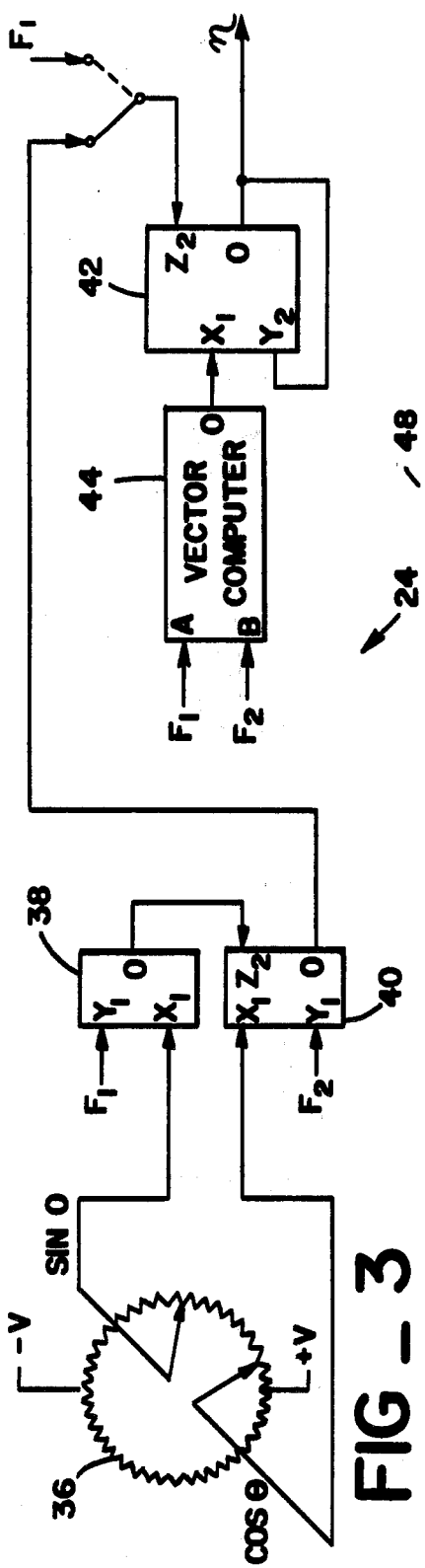
FIG_3
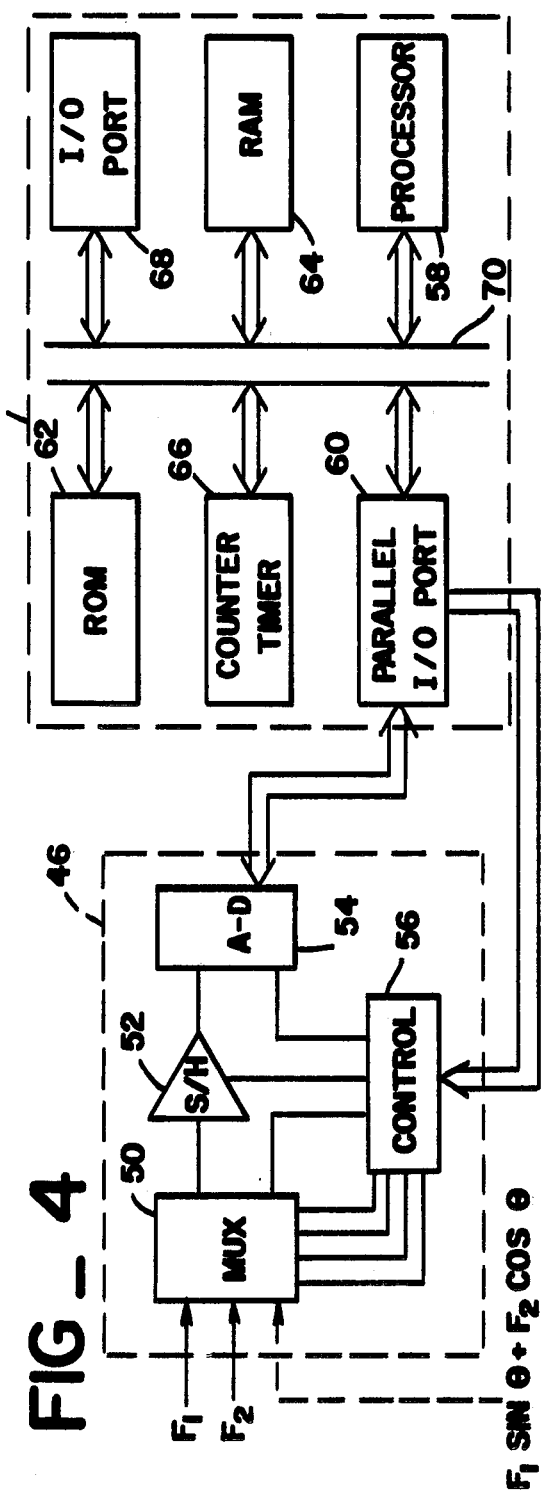
FIG_4

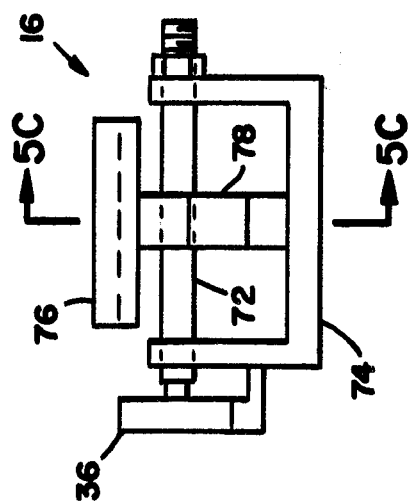
FIG_5B
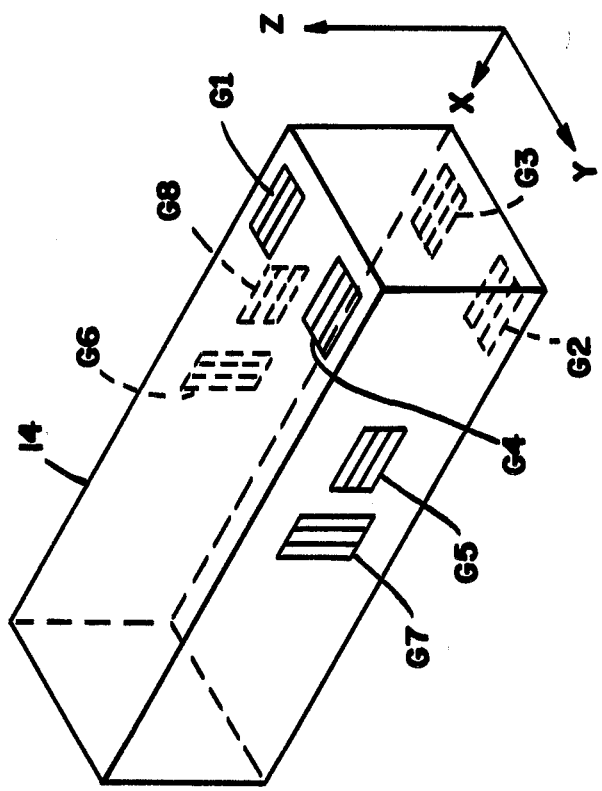
FIG_5A
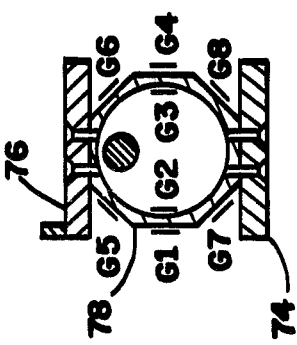
FIG_5C

FIG _ 6A
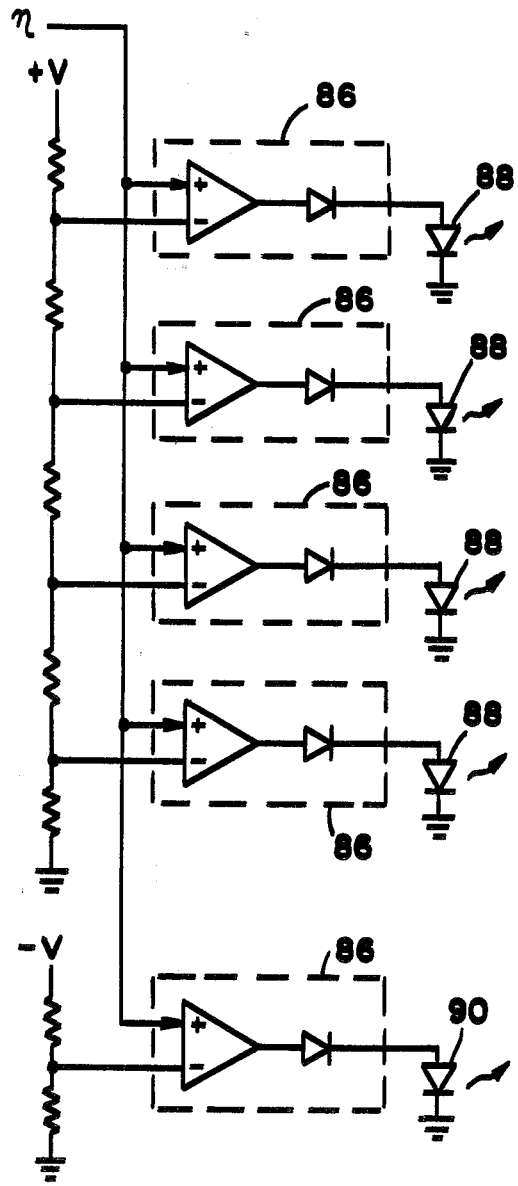
FIG _ 6B
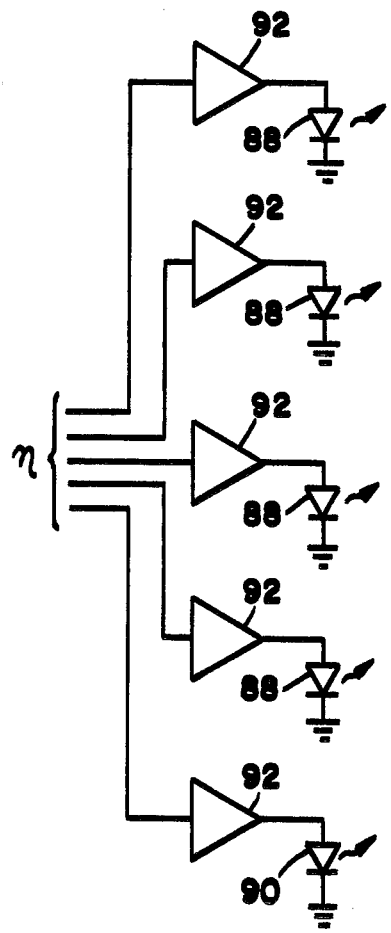
FIG _ 6C

PEDALLING EFFICIENCY INDICATOR

DESCRIPTION

1. Technical Field

The present invention relates generally to instrumentation and more particularly to a pedalling efficiency indicator for providing a human responsive form of quantitative measurement of pedalling efficiency for a pedacycle.

2. Background Art

As fossil fuel supplies diminish, modes of human transport offering alternatives to the internal combustion engine are receiving greater emphasis in research and development. It is well known that the human pedacycle system is a very efficient form of transportation. The energy a pedacyclist expends is derived ultimately from the sun through the nourishment the pedacyclist consumes. Thus, not only is the pedacycle an energy efficient transportation alternative, but is also linked to a renewable energy source. Pedacycle mechanics and human powered vehicle research can lead to a significant alleviation from dependence on fossil fuel. By way of example, a bicyclist may achieve during flat road riding at an average speed of 38 kph (23.75 mph) an equivalent energy expenditure of 370 kpl (870 mpg) of gasoline based on the bicyclist's caloric expenditure. Such equivalent calculations are disclosed in a printed publication by Whitt entitled, "Estimation of the Energy Expenditure of Sporting Cyclists", in Ergonomics, Volume 14, No. 2, May 1971, pages 419–429.

A typical pedacycle includes a crank set having a pair of crank arms and a pair of pedals, each pedal being rotatably mounted to a distal end of a different one of each of the crank arms. The highest pedalling efficiency is achieved when the force exerted by a foot of the pedacyclist on the pedal is normal to the crank arm. However, most pedacyclists, especially racing or professional cyclists, typically rely on training to increase strength and stamina rather than on improved pedalling technique.

Pedalling technique may be improved by obtaining a detailed knowledge of foot pedal interaction loads, with measurable variables being pedal load, angle of the crank arm relative to a vertical line, and the relative angle between a line normal to the pedal platform and the crank arm associated with each pedal. As a pedacyclist improves pedalling technique, power output capability is increased and muscle fatigue is minimized.

The knowledge of foot pedal interaction loads is also relevant in related aspects of pedacycling. In one aspect of pedacycling, overuse injuries to the pedacyclist may occur when musculoskeletal components are forced to carry loads incompatable with their strength and function. It has been suggested by Maury L. Hull, one of the coinventors herein, in a printed publication entitled, "Biomechanics of Lower Extremity Injuries in Human Powered Transportation", Proceedings Sixth New England Bioengineering Symposium, Pergamon Press, 1978, pages 51–54, that injuries can be prevented by judicious adjustment of foot pedal interaction loads because these ultimately dictate the musculoskeletal component loads. As described therein, a pattern recognition scheme based on features of the foot pedal interaction load profiles may be used to diagnose overuse injuries and recommend corrective adjustments.

In another aspect of pedacycling, the foot pedal interaction loads may be useful in the design of pedacycle frames and equipment (e.g., pedals, cranks, chains, etc.), as in Rory R. Davis and Maury L. Hull, the co-inventors herein, in a printed publication entitled, "Design of Aluminum Bicycle Frames", appearing recently in ASME Journal of Mechanical Design, have shown that frame stresses are sensitive to the magnitude of the foot pedal interaction loads, and accurate and complete stress analysis is necessary to design successsfully innovative bicycle frames from materials other than steel.

The foot pedal interaction loads have been used to study the mechanics of pedacycling as in R. J. Gregor, "Of Biomechanical Analysis of Lower Limb Action During Cycling at Four Different Loads", PhD. thesis, physical education, The Pennsylvania State University, 1976 and in P. D. Soden and B. A. Adeyefa, "Forces Applied to a Bicycle During Normal Cycling", Journal of Biomechanics, Volume 12, 1979, pages 527–541. Dynamometers integral within each of the pedals measured loads induced on the pedals by the pedacyclist. The pedal load data provided valuable information regarding the mechanics of pedalling. However, limitations arose from measuring only normal and tangential pedal loads, from riding a stationary pedacycle laterally supported which may not simulate actual pedacycling, and from not measuring absolute pedal position.

SUMMARY OF THE INVENTION

It is an object of the present invention to provide a pedalling efficiency indicator for measuring pedalling efficiency of a pedacyclist to evaluate pedalling technique.

It is a further object of the present invention to provide a pedalling efficiency indicator which is small and compact enough for mounting to a pedacycle to indicate a constant measuring of pedalling efficiency to the pedacyclist.

It is yet another object of the present invention to provide a pedalling efficiency indicator to enable a pedacyclist to evaluate on the road pedalling technique.

According to the present invention, a pedalling efficiency indicator for a pedacycle includes means for measuring a first force being applied normally to a selected one of a crank arm and a pedal of a crank set of the pedacycle. The crank set defines an axis, and the first force lies in a plane perpendicular to the axis. The measuring means is further for measuring a second force being tangential to the selected one of the crank arm and the pedal. The measuring means is operative to develop a first and a second signal commensurate with each of the first and second force, respectively. Means responsive to each of the first and second signals computes a measurement of pedalling efficiency determined from each of the first force and the second force.

In one aspect of the present invention, the measurement of pedalling efficiency is defined by a ratio of a torque applied to the selected one of the crank arm and the pedal and a resultant load on the selected one of the crank arm and the pedal.

In yet another aspect of the present invention, the pedalling efficiency indicator further includes means for indicating in human responsive form the measurement of pedalling efficiency. Computing means develops a third signal commensurate with the measurement made of pedalling efficiency. The indicating means is responsive to a third signal.

BRIEF DESCRIPTION OF THE DRAWINGS

FIGS. 1A and 1B illustrate a portion of a pedacycle and the definition of the forces used to derive the equations for a measurement of pedalling efficiency;

FIG. 2 is a schematic block diagram of one embodiment of a pedalling efficiency indicator according to the principles of the present invention;

FIG. 3 is one embodiment of a more detailed representation of the computer of FIG. 2;

FIG. 4 is another embodiment of a more detailed representation of the computer of FIG. 2;

FIGS. 5A, 5B and 5C illustrate the location of strain gauges shown in FIG. 2 to measure forces on the crank arm and pedal of FIGS. 1A and 1B; and FIGS. 6A and 6B illustrate an audible embodiment and a visual embodiment, respectively, of the indicator of FIG. 2. FIG. 6C illustrates a digital embodiment of FIG. 6B.

DETAILED DESCRIPTION OF THE DRAWINGS

Referring now to FIGS. 1A and 1B, there is shown a broken away portion of a pedacycle 10 including a crankset 12 being rotatably mounted in pedacycle 10 and defining an axis Y about which crankset 10 rotates. Crankset 12 has a crank arm 14 generally extending radially from axis Y and the pedal 16 being rotatably mounted to a distal end 18 of crank arm 14 and extending axially outwardly therefrom.

The representation of pedacycle 10 as shown in FIG. 1A is used to derive the equation for pedalling efficiency when measuring the forces upon crank arm 14, the normal component of force being shown as $F_{1A}$ and the tangential component of force being shown as $F_{2A}$ and drawn to a point where pedal 16 is mounted to distal end 18.

The representation of pedacycle 10 as shown in FIG. 1B is used to derive the equation of pedalling efficiency when measuring the forces upon pedal 16, the normal component to pedal 16 being shown as $F_{1B}$ and the tangential component to pedal 16 being shown as $F_{2B}$. As hereinafter described, an angle $\theta$ is measured between the direction of application of the normal component of force $F_{1B}$ to pedal 16 and crank arm 14.

A measurement of pedalling efficiency is defined by a ratio of a torque applied to a selected one of crank arm 14 and pedal 16 and a resultant load on the selected one of crank arm 14 and pedal 16. The torque on crank arm 14 is measured directly by force $F_{1A}$ and resultant load is measured from the square root of the sum of the squares of the first force $F_{1A}$ and the second force $F_{2A}$. The measurement of pedalling efficiency may be given by the equation $$\eta = \frac{F_{1A}}{(F_{1A}^2 + F_{2A}^2)^{\frac{1}{2}}}$$

The torque on pedal 16 is measured from the sum of the first force $F_{1B}$ multiplied by the sine of the angle $\theta$ between crank arm 14 and the direction of first force $F_{1B}$ and the second force $F_{2B}$ multiplied by the cosine of the angle $\theta$ between crank arm 14 and the direction of first force $F_{1B}$. The resultant load is measured from the square root of the sum of the squares of the first force $F_{1B}$ and the second force $F_{2B}$. Thus the measurement of pedalling efficiency may be given by the equation $$\eta = \frac{F_{1A}\sin\theta + F_{2A}\cos\theta}{(F_{1A}^2 + F_{2A}^2)^{\frac{1}{2}}}$$

Referring now also to FIG. 2, there is shown a pedalling efficiency indicator 20 according to the principles of the present invention. Pedalling efficiency indicator 20 comprises means 22 for measuring first force $F_1$ and second force $F_2$. As shown in FIG. 2, each of first force and second force, $F_1$ and $F_2$, refer to the respective forces $F_{1A}$ and $F_{2A}$ or $F_{1B}$ and $F_{2B}$, respectively, should the forces be measured as applied to the selected one of crank arm 14 or pedal 16. Pedalling efficiency indicator 20 further comprises means 24 for computing measurement of pedalling efficiency determined from each of first force $F_1$ and second force $F_2$. Measuring means 22 is operative to develop a first signal commensurate with first force $F_1$ and a second signal commensurate with second force $F_2$. Computing means 24 is responsive to each of the first signal and the second signal and responsive thereto.

Measuring means 22 includes a first strain gauge ring 26 and a second strain gauge ring 28. First strain gauge ring 26 has strain gauges G1, G2, G3 and G4 arranged to measure the first force $F_1$. The second strain gauge ring 28 has strain gauges G5, G6, G7 and G8 arranged to measure second force $F_2$. Measuring means 22 further includes a first filter 30 and a second filter 32. First filter 30 is associated with first strain gauge ring 26. Second filter 32 is associated with second strain gauge ring 28.

A voltage regulator 34 provides well regulated voltages $+V$ and $-V$ to supply reference voltages for each of first strain gauge ring 26 and second strain gauge ring 28. Additionally, voltage regulator 34 may also provide the supply voltages for other active circuit elements of pedalling efficiency indicator 20. Furthermore, each of first strain gauge ring 26 and second strain gauge ring 28 need only be supplied by one of the supply voltages $+V$ or $-V$ as each of first strain gauge ring 26 and second strain gauge ring 28 are arranged within balanced Wheatstone bridge circuits. A deviation from the normal balance voltage from each Wheatstone bridge circuit indicates the presence of each force $F_1$ and $F_2$.

The output voltages from each of first strain gauge ring 26 and second strain gauge ring 28 are applied to first filter 30 and second filter 32. Typically each of first filter 30 and second filter 32 have a high impedance input amplifier for multiplying the voltages developed by the Wheatstone bridge circuits and an output low pass filter for filtering noise from such voltages. The first signal commensurate with first force $F_1$ and the second signal commensurate with second force $F_2$ are developed by first filter 30 and second filter 32, respectively. The low pass outputs of each of first filter 30 and second filter 32 may typically have a cutoff frequency of 20 hz.

Referring now to FIG. 3, there is shown a schematic block diagram of a first embodiment of computer 24 of FIG. 2 which includes a sine-cosine potentiometer 36, a first analog multiplier 38, a second analog multiplier 40, a third analog multiplier 42 and a vector computer 44.

Potentiometer 36 measures the angle between crank arm 14 and the normal component of force, $F_1$, on pedal 16, and develops a first output signal commensurate with sine $\theta$ and a second output signal commensurate with cosine $\theta$. Potentiometer 36 may typically be a model 106 20K potentiometer commercially available under the trade name Veretech.

Each of first, second and third analog multipliers 36, 38 and 40 have first inputs ($X_1$, $X_2$), second inputs ($Y_1$, $Y_2$), third inputs ($Z_1$, $Z_2$) and an output (O). The overall transfer function of each multiplier 36, 38 and 40 is given by $O=(X_1-X_2)(Y_1-Y_2)+Z_2$. Each of first, second and third analog multipliers 36, 38 and 40 may typically be AD534IC multipliers commercially available from Analog Devices.

First analog multiplier 38 has its input $X_1$ coupled to filter 30 (FIG. 2) for application of the first signal commensurate with $F_1$, and its input $Y_1$ coupled to potentiometer 36 for application of the first output signal commensurate with sine $\theta$. First analog multiplier 38 develops an output signal at its output O commensurate with $F_1 \sin \theta$.

Second analog multiplier 40 has its input $X_1$ coupled to filter 32 (FIG. 2) for application of the second signal commensurate with $F_2$, its input $Y_1$ coupled to potentiometer 36 for application of the second output signal commensurate with cosine $\theta$, and its input $Z_2$ coupled to output O of first analog multiplier 38 for application of the signal commensurate with $F_1 \sin \theta$.

As given by the hereinabove described transfer function, second analog multiplier 40 develops an output signal at its output O commensurate with $F_1 \sin \theta + F_2 \cos \theta$.

Vector computer 44 has a first input A, a second input B and an output O. The overall transfer function is given by $O=(A^2+B^2)^{\frac{1}{2}}$. Vector computer 44 may typically be an AD531 multiplier divider computation circuit commercially available from Analog Devices, and biased to provide the square root of the sum of the squares function as is known in the art.

Vector computer 44 has its input A coupled to filter 30 for application of the first signal commensurate with $F_1$ and its input B coupled to filter 32 for application of the second signal commensurate with $F_2$. As given by the hereinabove described transfer function for vector computer 44, a signal is developed at its output O commensurate with $(F_1^2+F_2^2)^{\frac{1}{2}}$.

Third analog multiplier 42 has its input $X_1$ coupled to output O of vector computer 44 for application of the signal commensurate with $(F_1^2+F_2^2)^{\frac{1}{2}}$, and its input $C_2$ coupled to the output O of second analog multiplier 40 for application of the signal commensurate with $F_1 \sin \theta + F_2 \cos \theta$. Furthermore, a feedback loop couples the output O to the input $Y_2$ of third analog multiplier 42 for providing a divider function known in the art. Third analog multiplier 42 develops at its output O an output signal commensurate with the measurement of pedalling efficiency $$\eta = \frac{F_1 \sin \theta + F_2 \cos \theta}{(F_1^2 + F_2^2)^{\frac{1}{2}}}$$

As hereinabove described, the expression $F_1 \sin \theta + F_2 \cos \theta$ is the torque upon crank arm 14 when measuring means 22 measures the normal and tangential forces, $F_{1B}$ and $F_{2B}$ (FIG. 1B), applied to pedal 16. Of course, if measuring means 22 measures the normal and tangential forces, $F_{1A}$ and $F_{2A}$ (FIG. 1A), applied to crank arm 14, the torque upon crank arm 14 is given directly by $F_{1A}$ and the circuitry described in reference to potentiometer 36 and first and second analog multipliers 38 and 40 need not be used, in which event the first signal commensurate with $F_{1A}$ may be directly applied to input $Z_2$ of third analog multiplier 42 which would then develop at its output O a signal commensurate with the measurement of pedalling efficiency given by:

$$\eta = \frac{F_1}{(F_1^2 + F_1^2)^{\frac{1}{2}}}$$

Referring now to FIG. 4, there is shown a schematic block diagram of a second embodiment of computer 24 of FIG. 2 which includes means 46 for converting the signal developed by first filter 30 commensurate with force $F_1$ and the signal developed by second filter 32 commensurate with second force $F_2$ to a digital signal and means 48 for processing the digital signal to compute the measurement of pedalling efficiency. Converting means 46 includes a time division multiplexer 50, a sample/hold amplifier 52, an analog to digital converter 54 and a controller 56. Processing means 48 includes processor 58, first input/output (I/O) port 60, read only memory (ROM) 62, a random access memory (RAM) 64, a counter/timer 66, a second input/output (I/O) port 68 and a data bus 70.

The signals from measuring means 22 commensurate with each of forces $F_1$ and $F_2$ are applied to multiplexer 50. As hereinabove described, the forces are measured on crank arm 14 (being $F_{1A}$ and $F_{2A}$) the inputs to multiplexer 50 need only be the signals commensurate with these forces. However, should the forces $F_1$ and $F_2$ be measured at pedal 16, multiplexer 50 requires an additional input of a signal commensurate with $F_1 \sin \theta + F_2 \cos \theta$ which may be developed as hereinabove described with reference to FIG. 3.

Multiplexer 50 develops a time divisioned multiplex signal which is applied to sample/hold amplifier 52 for subsequent application to analog digital converter 54 which converts the multiplexed signal to a digital signal. Controller 56 maintains timing and synchronization of multiplexer 50, sample/hold amplifier 52 and analog digital converter 54.

Under control of processor 58 and counter timer 66, the digital signal as applied to first input/output port 60 for application to data bus 70. The data is utilized by processsor 58 and may be stored in RAM 64. The programs for acquiring the digital data and computing the equations for pedalling efficiency are stored in RAM 62. The measurement of pedalling efficiency, when calculated by processor 58, is placed on bus 70 in digital form and applied to second I/O port 68. I/O port 68 develops a signal commensurate with the measurement of pedalling efficiency.

Referring now to FIG. 5A, there is shown a portion of crank arm 14 in the location of the strain gauges used in the Wheatstone bridge circuits of measuring means 22 (FIG. 2) to measure forces $F_{1A}$ and $F_{2B}$.

Referring now to FIGS. 5B and 5C, there is shown a specially constructed pedal 16 to measure forces $F_{1B}$ and $F_{2B}$ (FIG. 1B). Pedal 16 includes a spindle 72 for mounting distal end 18 of crank arm 14, a generally U-shaped pedal frame 74 rotatably mounted to spindle 72, a foot pad 76 to which forces $F_{1B}$ and $F_{2B}$ are applied, and the strain gauge dynamometer 78 coupled intermediately to frame 74 and foot pad 76. Potentiometer 36 is coupled to each of spindles 72 and pedal frame members 74. As best shown in FIG. 5C, the strain gauge locations of the Wheatstone bridge circuits of FIG. 2 are shown on dynamometer 78.

In practicing the present invention, it is useful to indicate to the user of pedacycle 10 a relative measurement of pedalling efficiency in human responsive form. Referring again to FIG. 2, pedalling efficiency indicator 20 may further include means 80 for indicating in human responsive form the measurement of pedalling efficiency, measuring means 79 being responsive to the signal developed by computer 24 commensurate with the measurement of pedalling efficiency.

Referring now to FIGS. 6A, 6B and 6C there are shown alternate embodiments of indicating means 80. In FIG. 6A, there is shown a voltage controlled oscillator (VCO) 82 and a speaker 84. The signal developed by computer 24 commensurate with the measurement of pedalling efficiency is applied to VCO 82 and develops an oscillating signal having a frequency determined by the voltage level of the output signal of computer 24. As an example, as pedalling efficiency is improved by the user of pedacycle 10, the output signal of computer 24 may increase in voltage, which in turn increases the frequency of the oscillating signal developed by VCO 82. The oscillating signal is applied to speaker 84 which develops an audio tone changing in frequency, the higher the pitch of the audio tone, the more efficient the pedalling techniques of the user of pedacycle 10.

The embodiment of indicating means 80 as shown in 6B includes a plurality of comparators 86, a plurality of photo emitting devices such as light emitting diodes 88 and an additional light emitting diode 90. All of diodes 88 and 90 are associated with a different one of each comparator 86. As in the above example, the voltage level of the output signal from computer 24 may increase as the measurement of pedalling efficiency increases. Each comparator 86 is biased to turn on at a different voltage level to forward bias one or more diodes 88 to emit light therefrom. Typically, diodes 88 may emit a green light. Thus, as more diodes 88 emit light, the user of pedacycle 10 realizes the measurement of pedalling efficiency has increased. Similarly, diode 90 may emit a light having a wavelength different from diodes 88, such as red. The low voltage level of the output signal from comparator 24 will turn on comparator 86 associated with diode 90 passing a current through diode 90 to warn the user of pedacycle 10 of an inefficient pedalling technique.

The embodiment of indicator means 80 shown in FIG. 6C is useful when the measurement of pedalling efficiency developed computer 24 is a digital signal. Indicator means 80 in the FIG. 6C embodiment includes a plurality of amplifier/drivers 92, and a plurality of photo emitting devices such as the array of light emitting diodes 88 and 90 shown in FIG. 6B. By way of example, as pedalling efficiency increases the measurement of pedalling efficiency developed by computer 24 as a digital signal will increase the number of bit positions which may have a logical one. As the logical one is applied to amplifier drivers 92, one or more light emitting diodes 88 are forward biased and emit a green light to indicate to the user of pedacycle 10 that the measurement of pedalling efficiency has increased. One such bit position may also contain a logical one to indicate a very low measurement of pedalling efficiency to be applied to the amplifier driver 92 associated with diode 90 to forward bias diode 90 and emit a red light therefrom giving such an indication to the user of pedacycle 10.

The present invention has been described herein with reference to preferred embodiments thereof. It is now obvious to those skilled in the art to make numerous uses of and modifications to the preferred embodiment of the present invention without departing from the inventive concepts disclosed herein. The present invention is defined by and limited only by the scope of the appended claims which hereinafter follow.

I claim:

1. For a pedacycle of the type including a crankset being rotatably mounted in said pedacycle and defining an axis, said crankset having a crank arm generally extending radially from said axis and a pedal being rotatably mounted to a distal end of said crank arm and extending axially outwardly from said crank arm, a pedalling efficiency indicator comprising:

means for measuring a first force being normal to a selected one of said crank arm and said pedal and being in a plane perpendicular to said axis, and further for measuring a second force being tangential to said selected one of said crank arm and said pedal; and means for computing pedalling efficiency as a function of said first force and said second force.

2. A pedalling efficiency indicator in accordance with claim 1 wherein said pedalling efficiency is computed as a ratio of the resultant normal force applied to said crank arm by said first force and said second force to the resultant load on said selected one of said crank arm and said pedal.

3. A pedalling efficiency indicator in accordance with claim 2 wherein the resultant normal force is calculated directly from said first force, and said load is calculated from the square root of the sum of the squares of said first force and said second force, said selected one being said crank arm.

4. A pedalling efficiency indicator in accordance with claim 3 wherein the computation of pedalling efficiency $\eta$ as a function of said first force $F_1$ and said second force $F_2$ is given by the equation:

$$\eta = \frac{F_1}{(F_1^2 + F_2^2)^{\frac{1}{2}}}$$

5. A pedalling efficiency indicator in accordance with claim 2 wherein the resultant normal force is calculated from the sum of said first force multiplied by the sine of the angle between said crank arm and the direction of said first force and said second force multiplied by the cosine of the angle between said crank arm and the direction of said first force, and said load is calculated from the square root of the sum of the squares of said first force and said second force, said selected one being said pedal.

6. A pedalling efficiency indicator in accordance with claim 5 wherein the computation of pedalling efficiency $\eta$ as a function of said first force $F_1$ and said second force $F_2$ is given by the equation:

$$\eta = \frac{F_1 \sin\theta + F_2 \cos\theta}{(F_1^2 + F_2^2)^{\frac{1}{2}}}$$

wherein $\theta$ is the angle between said crank arm and the direction of said first force.

7. A pedalling efficiency indicator in accordance with claim 1 or 4 wherein said computing means includes:

means for developing a first signal and a second signal as a function of said first force and said second force, respectively;

means for converting said first signal and said second signal to a digital signal; and means for processing said digital signal to compute pedalling efficiency.

8. A pedalling efficiency indicator in accordance with claim 1 or 4 wherein said computing means includes:

means for developing a first signal and a second signal as a function of said first force and said second force, respectively;

first analog circuit means responsive to each of said first signal and said second signal for computing the square root of the sum of the squares of said first force and said second force and operative to develop a third signal commensurate with said square root; and second analog circuit means responsive to each of said first signal and said third signal for computing a division of said first force by said square root.

9. A pedalling efficiency indicator in accordance with claim 1 or 6 wherein said computing means includes:

means for developing a first signal and a second signal as a function of said first force and said second force, respectively;

means for determining the angle between said crank arm and the direction of said first force, said first force being applied normal to said pedal, and operative to develop a third signal commensurate with the sine of the angle and a fourth signal commensurate with the cosine of the angle;

means for converting each of said first signal, said second signal, said third signal and said fourth signal to a digital signal; and means for processing said digital signal to compute pedalling efficiency.

10. A pedalling efficiency indicator in accordance with claim 1 or 6 wherein said computing means includes:

means for developing a first signal and a second signal as a function of said first force and said second force, respectively;

means for determining the angle between said crank arm and the direction of said first force, said first force being applied normal to said pedal, and operative to develop a third signal commensurate with the sine of the angle and a fourth signal commensurate with the cosine of the angle;

first analog circuit means responsive to each of said first signal, said second signal, said third signal, and said fourth signal for computing the sum of said first force multiplied by the sine of the angle between said crank arm and the direction of said first force and said second force multiplied by the cosine of the angle between said crank arm and the direction of said first force and operative to develop a fifth signal commensurate with the sum computed by said first analog circuit means;

second analog circuit means responsive to each of said first signal and said second signal for computing the square root of the sum of the squares of said first force and said second force and operative to develop a sixth signal commensurate with the square root; and third analog circuit means responsive to each of said fifth signal and said sixth signal for computing the ratio between the sum of said first analog circuit means and the square root.

11. A pedalling efficiency indicator in accordance with claim 1 wherein said indicator further comprises:

means for visually indicating the resultant computation of pedalling efficiency.

12. A pedalling efficiency indicator in accordance with claim 11 wherein said computing means further develops a signal as a function of said pedalling efficiency, said indicating means being responsive to said signal.

13. A pedalling efficiency indicator in accordance with claim 14 where said indicating means includes:

a plurality of photo emitting devices; and a plurality of comparators, each of said comparators associated with a different one of each of said devices, said signal being applied to each of said comparators, each of said comparators developing an on signal in response to a different one of preselected levels of said signal, said on signal developed by each comparator being applied to one of said devices associated therewith.

14. A pedalling efficiency indicator in accordance with claim 12 wherein said indicating means includes:

means responsive to said signal for developing an oscillating signal having a frequency determined by said signal; and means responsive to said oscillating signal for emitting an audio tone having a frequency determined by said oscillating signal.

* * * * *